United States Patent
Heinonen et al.

(10) Patent No.: US 6,892,726 B1
(45) Date of Patent: May 17, 2005

(54) ARRANGEMENT IN CONNECTION WITH EQUIPMENT USED IN PATIENT CARE

(75) Inventors: Erkki Heinonen, Helsinki (FI); Pekka Meriläinen, Helsinki (FI); Antti Särelä, Espoo (FI); Mario Loncar, Ekerö (SE)

(73) Assignee: Instrumentarium Corp., Helsinki (FI)

( * ) Notice: Subject to any disclaimer, the term of this patent is extended or adjusted under 35 U.S.C. 154(b) by 0 days.

(21) Appl. No.: 09/857,681
(22) PCT Filed: Dec. 3, 1999
(86) PCT No.: PCT/FI99/01006

§ 371 (c)(1),
(2), (4) Date: Sep. 4, 2001

(87) PCT Pub. No.: WO00/33903
PCT Pub. Date: Jun. 15, 2000

(30) Foreign Application Priority Data

Dec. 8, 1998 (FI) .................................................. 982652

(51) Int. Cl.[7] ............................................. A61M 16/00
(52) U.S. Cl. ........................... 128/202.22; 128/204.21; 128/204.23
(58) Field of Search ....................... 128/202.22, 204.21, 128/204.23, 203.12, 203.14

(56) References Cited

U.S. PATENT DOCUMENTS

| | | | |
|---|---|---|---|
| 4,366,821 A | | 1/1983 | Wittmaier et al. ........... 600/532 |
| 4,651,729 A | | 3/1987 | Rae ......................... 128/203.14 |
| 4,934,358 A | * | 6/1990 | Nilsson et al. ............ 128/202.22 |
| 5,057,822 A | * | 10/1991 | Hoffman ................. 128/202.22 |
| 5,094,235 A | * | 3/1992 | Westenskow et al. ..... 128/203.12 |
| 5,320,092 A | * | 6/1994 | Ryder ..................... 128/202.22 |
| 5,331,995 A | | 7/1994 | Westfall et al. ................. 137/8 |
| 5,363,842 A | * | 11/1994 | Mishelevich et al. .... 128/204.23 |
| 5,365,922 A | * | 11/1994 | Raemer ................. 128/202.22 |
| 5,626,131 A | | 5/1997 | Chua et al. ............. 128/204.23 |
| 5,865,174 A | | 2/1999 | Kloeppel ................ 128/204.23 |

FOREIGN PATENT DOCUMENTS

| | | |
|---|---|---|
| EP | 720858 | 7/1996 |
| EP | 722748 | 7/1996 |
| EP | 835672 | 4/1998 |
| GB | 1294808 | 11/1972 |
| WO | 87/06142 | 10/1987 |
| WO | 98/31282 | 7/1998 |

OTHER PUBLICATIONS

Westenskow D., *Closed Loop Control of Blood Pressure, Ventilation, and Anesthesia Delivery*, Int Journal of Clinical Monitoring and Computing 4: 69–74, 1987.

Mason D.G. et al, *Development of a Portable Closed–Loop Atracurium Infusion System, System Methodology and Safety Issues*, International Journal of Clinical Monitoring and Computing 13: 243–252, 1997.

* cited by examiner

Primary Examiner—Aaron J. Lewis
(74) Attorney, Agent, or Firm—Andrus, Sceales, Starke & Sawall, LLP

(57) ABSTRACT

The invention relates to an arrangement in connection with equipment used in patient care, the arrangement comprising a controllable device (2a, 2b), a measuring device (5a, 5b) adapted to measure a measuring signal dependent on the controllable parameter, a measuring point of the measuring signal, a transmission link (21, 22) between the measuring point of the measuring signal and the measuring device, which transmission link requires a separate connection, whereby the measuring device (5a, 5b) is adapted to convert the measuring signal into measuring value which correlates with the operation of the controllable device, and the arrangement further comprising a user interface (20) and a control unit (7a, 7b) adapted to control the controllable device on the basis of the measuring value and the set values. To minimize damages, the arrangement is adapted to compare the measuring value with the reference value of the environment and the control unit (7a, 7b) is adapted to disconnect the control of the controllable device (2a, 2b) based on the measuring value when the measuring value obtains a reference value.

11 Claims, 2 Drawing Sheets

ARRANGEMENT IN CONNECTION WITH EQUIPMENT USED IN PATIENT CARE

CROSS REFERENCE TO RELATED APPLICATION

The present application is the U.S. national stage application of International Application PCT/FI99/01006, filed Dec. 3, 1999, which international application was published on Jun. 15, 2000 as International Publication WO 00/33903 in the English language. The International Application claims the priority of Finnish Patent Application No. 982652 filed Dec. 8, 1998.

SUMMARY OF THE INVENTION

The invention relates to an arrangement in connection with equipment used in patient care, the arrangement comprising a controllable device adapted to affect a controllable parameter required in patient care to provide care or some other nursing procedure, a measuring device adapted to measure a measuring signal dependent on the controllable parameter, a measuring point of the measuring signal, which measuring point is outside the controllable device, a transmission link between the measuring point of the measuring signal and the measuring device, which transmission link requires a separate connection, whereby the measuring device is adapted to convert the measuring signal into a measuring value which correlates with the operation of the controllable device, and the arrangement further comprising a user interface, by which the controllable device can be controlled using set values, and a control unit adapted to control the controllable device on the basis of the measuring value and the set values.

A basic requirement set for devices used in patient care is that they are safe and operationally reliable in the normal use of the device, or when a user unintentionally causes malfunctions or in any one-fault situation of the device.

As examples of the above mentioned devices for patient care, gas mixers and ventilators used in intensive care and anaesthesia can be mentioned. A patient is treated by connecting him by means of a patient circuit to the device used for patient care, e.g. to a combination of a gas mixer and ventilator. From the patient circuit there is a measuring connection to a monitor which monitors the condition of a patient. Using measuring information the monitor provides a person nursing the patient supervises the condition of the patient and adjusts set values of the device used in patient care so that the measuring information corresponds to the desired value of the moment.

The control has the characteristic of indirectly affecting the measuring values through the set values of the device used in patient care. Typical of the control is also its long-term effect. Some of these indirect pairs of measuring values and set values are listed in the table below, which also includes a reference value for each parameter, which reference value is measured when the measuring signal comes from the environment, and not from the patient circuit.

The indirectness between the measuring parameters and the set value affecting these parameters can even be doubled. For example, blood pressure can be regulated by means of anaesthetic concentration of the exhalation, whereby the anaesthetic concentration in turn is controlled by means of the anaesthetic concentration of an anaesthesia vaporizer of the gas mixer according to the table below.

| Measuring value | Operative set value | Reference value of environment |
|---|---|---|
| Anaesthetic gas concentration of respiration | Anaesthetic concentration of anaesthetic vaporizer of gas mixer and gas flow of gas mixer | 0% |
| Oxygen concentration of respiration | Oxygen flow of gas mixer | 21% |
| Nitrous oxide concentration of respiration | Nitrous oxide flow of gas mixer | 0% |
| Carbon dioxide concentration of respiration | Minute ventilation of ventilator | 0% |
| Airway pressure of patient | Respiration volume of ventilator | 0 |
| Patient flow | Gas flow of ventilator | 0 |

Due to indirectness and a long time constant, the exact adjustment of measuring values is slow and difficult, which leads to variation in patient values. This in turn may have harmful effects on the end result of nursing.

To improve the above situation, a variety of solutions have been suggested for automatizing the control loop. In such a system, a controller, instead of a person taking care of the patient, closes the control system between the measuring value and the set value of the device for patient care.

The controller is capable of considering the effects of prevailing indirectnesses and the control time constant and thus of automatically optimising the set value. With such a system in use, a person nursing the patient only needs to set a desired value into the control system.

U.S. Pat. No. 5 094 235, for example, describes an automatized control system as described above. In addition, several examples can be found in literature which prove the superiority of an automatized control system over a nursing person in achieving and maintaining patient values. As an example, the publication Westenskow D., Closed loop control of blood pressure, ventilation, and anesthesia delivery, Int Journal of Clinical Monitoring and Computing 4: 69–74, 1987 can be mentioned. In spite of this, feedback control systems described above have not become more common in nursing environments. One reason why the solutions, practicable as such, have remained at exploratory and experimental stages are safety and reliability requirements set for the equipment. The problem has been acknowledged, and the research relating to the field is about to move over from estimations of controllers' practicability to safety questions. The publication Mason D. G. et al., Development of a portable closed-loop atracurium infusion system, systems methodology and safety issues, International Journal of Clinical Monitoring and Computing 13: 243–252, 1997 can be mentioned as an example of the above factors. The automatic feedback complicates the system and brings new possibilities of fault situations, the existence of which should be taken into account when implementing the equipment.

The monitor measures the actual patient values either close to a patient or by means of a sensor attached to the patient. In a closed-loop control system, a potential breaking of the measuring connection with the patient also nullifies the effect of the set value of the device for patient care on the measuring value, since the monitor cannot observe what happens at the measuring point. This can lead to dosing mistakes, which may quickly have harmful consequences.

BRIEF DESCRIPTION OF THE INVENTION

The object of the invention is to provide an arrangement by which the safety risk, which is substantially present in the prior art, can be eliminated. This is achieved by the arrangement according to the invention, which is characterized in that the arrangement is adapted to compare the measuring value with a reference value of the environment and that the control unit is adapted to disconnect the control of the controllable device based on the measuring value when the measuring value obtains a reference value.

The invention has especially the advantage that the breaking of the measuring connection can be detected by means of the invention. When the arrangement of the invention detects a fault situation, it is capable of automatically switching off the feedback control system and giving an alarm about the need for fixing the situation, if necessary. An advantage of the invention is also its simplicity, whereby the introduction of the invention becomes advantageous.

BRIEF DESCRIPTION OF THE DRAWING

In the following the invention will be described in greater detail by means of a preferred embodiment illustrated in the attached drawings, in which.

DETAILED DESCRIPTION OF THE INVENTION

Figure 1:
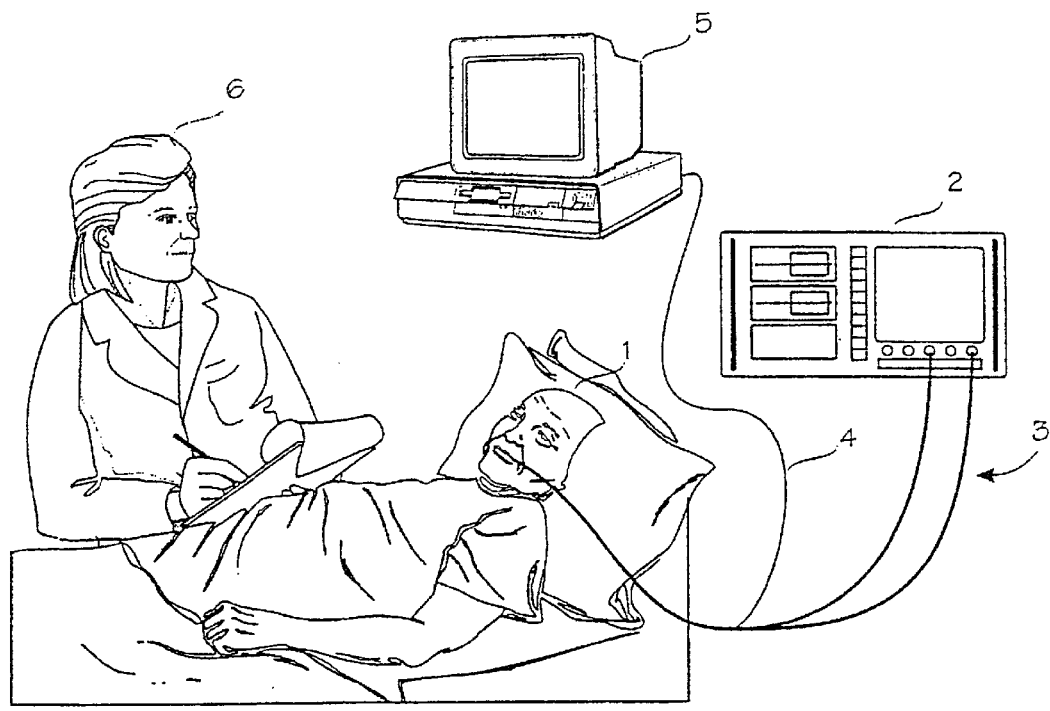
FIG. 1 shows a schematic view of an operational environment of equipment used in patient care.

FIG. 1 shows schematically an operational environment of equipment used in patient care. In FIG. 1, a patient 1 is connected via a patient circuit to a device 2 used in patient care, which, in the example of the figure, is a combination of a gas mixer and ventilator. From the patient circuit 3 there is a measuring connection 4 to a monitor 5 which monitors the condition of the patient. A nursing person 6 supervises the condition of the patient on the basis of the measuring information obtained from the monitor and adjusts set values of the device 2 such that the measuring information corresponds to the desired value of the moment, as explained above. The term patient care covers herein both the actual treatment and the nursing procedures, e.g. examinations, follow-up, various measurements etc.

Figure 2:
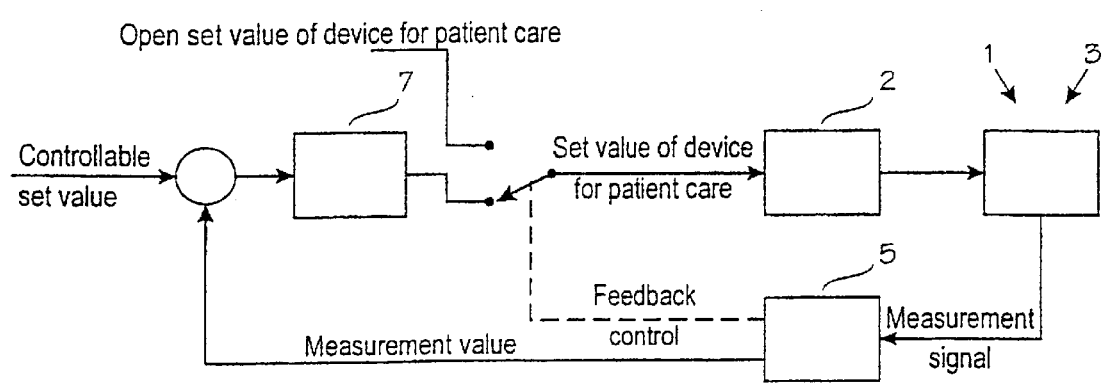
FIG. 2 shows a diagram of a feedback control system.

FIG. 2 shows a feedback control system. The device 2 used in patient care in the system affects the controllable parameter required in patient care to provide care in a required way. A measuring device measures a measuring signal from the controllable parameter either directly or indirectly by means of the effect caused by the treatment system and the patient. The measuring signal in question is converted to a measuring value in a monitor 5. In FIG. 2, a patient and patient circuit share the same block. The measuring value is fed back to the device 2 for patient care in such a manner that the device can, by comparing the measuring value with the desired set value, control the device 2 for patient care such that the set value is achieved in the most preferable manner in regard to the patient and kept at the desired value. The reference number 7 in FIG. 2 refers to a controller. The measuring of the measuring value requires that a separate measuring sensor or a transmission link of a measuring signal is arranged between the measuring device, i.e. the monitor, and the measuring point, whereby the feedback is performed on the basis of the actual value measured from the patient. While being controlled, the measuring value has the characteristic of obtaining a value that differs from the reference value of the environment. The reference value of the environment is a known value which can be fed to the control unit in a suitable manner, for example. Examples of reference values of the environment are shown in the table above. The above factor is applied in the invention for example in such a manner that in order to perform feedback, the measuring value has to differ from the reference value of the environment, and vice versa, feedback disconnects itself automatically if the measuring value is returned to the reference value of the environment. When the feedback is disconnected, the device 2 for patient care may continue its operation either by internal sensors or even without sensors based on a calibrated set value of the controllable device. In such a case, however, the set value may differ from the situation in which the feedback is based on the signal measured from the patient. When, for example, the anaesthetic concentration is regulated on the basis of a patient signal, the set value may be either the concentration of inhalation or exhalation. When the feedback is disconnected, the set value is the anaesthetic concentration of fresh gas inside the apparatus.

The disconnection of feedback described above may also occur intrinsic to respiration, if the respiration period includes a stage at which the measuring signal corresponds to the reference signal of the environment. When the flow to the patient is thereby regulated, for instance, the control is carried out by means of internal sensors at the beginning of the respiration. When the flow begins and the sensor measuring the patient value detects this flow, the feedback from the patient value is switched on. Correspondingly, when airway pressure is controlled while patient pressure equals zero, e.g. at the end of exhalation, a new inhalation is started by means of internal sensors of the device used for patient care. The switching on and off of the patient sensors in such cases are, however, transparent to the care when the signal measured by the device for patient care corresponds to that measured from the patient.

Figure 3:
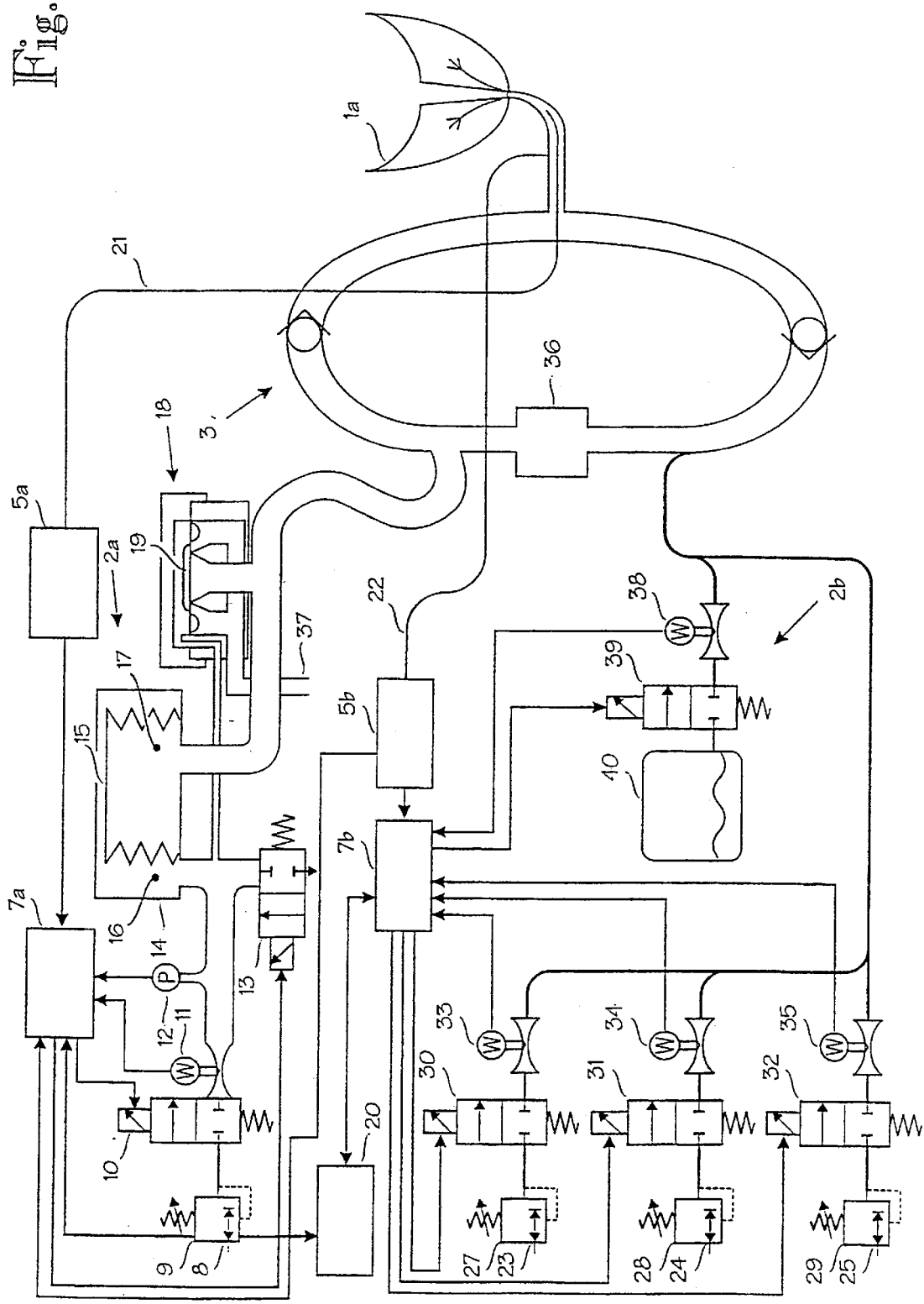
FIG. 3 shows a diagram of a preferred embodiment of an arrangement according to the invention.

FIG. 3 shows a preferred embodiment of an arrangement according to the invention. The example of FIG. 3 illustrates an arrangement used in anaesthesia for maintaining a patient's vital functions, the arrangement comprising a ventilator 2a, gas mixer 2b, patient circuit 3 connecting the ventilator and gas mixer into the patient's lungs 1a, patient pressure and flow monitoring 5a and gas monitor 5b measuring patient gases.

The ventilator comprises a control unit 7a, regulating unit of drive gas comprising a reception coupling 8 of pressurized drive gas, pressure regulator 9 of drive gas, inhalation valve 10, flow measurement 11 of drive gas, measurement 12 of drive gas and exhalation valve 13. The regulating unit of drive gas guides gas into a container 14 which is divided by a movable wall 15 into a drive gas space 16 and patient gas space 17.

The ventilator is operated such that the ventilator control unit controls the regulating unit of drive gas, which doses drive gas into the drive gas space 16, while the exhalation valve is closed. As drive gas volume increases, the patient gas space 17 on the other side of the movable wall decreases. The gas flows out of the patient gas space 17 via the patient circuit 3 into the patient's lungs 1a, which, being elastic, are expanded, and the patient inhales. Due to elasticity of lungs 1a, as the amount of gas in the circuit increases, the prevailing pressure in the circuit increases as well. Inhalation stops when the ventilator control unit 7a closes the drive gas valve and opens the exhalation valve 13. Then the gas flows out from the drive gas space 16 and the elasticity of lungs 1a contributes to the decrease in the volume of the lungs by moving the movable wall 15 by means of the patient circuit and by thus increasing the patient gas space 17 in the container. As the movable wall 15 comes to its extreme position, overpressure, which still potentially exists in the patient circuit, opens a valve element 19 of an overflow valve 18 and lets the gas flow either into the surrounding air or into a gas outlet system through a junction 37.

The drive gas regulation control of the ventilator control unit 7a is, on the one hand, based on the user-set values that are achieved from the user interface 20, on internal sensors 11, 12 of the ventilator and on the measuring values measured by monitors 5a, 5b from the patient. In the example of FIG. 3, a monitor 5a measuring airway pressure of a patient and patient flow is connected to a measuring point near the patient by a signal line 21. Said signal line can be either pneumatic, when the electric sensor itself is in the monitor 5a, or electric, whereby the actual sensor is brought to the measuring point. The signal line 21 comprises one or more signal conductors.

The monitor 5b measuring patient gases is connected via a signal line 22 to the measuring point. This line, too, may be either electric or pneumatic depending on the actual location of the measuring sensor. The solution according to the invention is not confined to the implementation of a signal line. In addition, a signal line can also be a wireless connection based on e.g. electromagnetic radiation, an optical connection etc.

A patient circuit obtains patient gas via the gas mixer 2b. Controlled by the control unit 7b of the gas mixer, the gas mixer 2b mixes a gas mixture, or fresh gas, composed of gases connected to inlet connectors 23, 24, 25 of pressurized gas into the patient circuit 3. Mixing is done by controlling a flow regulating valve 30, 31, 32 connected after pressure regulators 27, 28, 29 arranged to each gas line and a flow meter 33, 34, 35 in the line. The control unit 7b of the gas mixture regulates the concentration and total flow of different gases in the mixture by means of the above elements. The control is performed on the basis of the set values obtained from the user interface 20, on the one hand, and of the internal sensor values of the device and patient values measured from the patient, on the other hand. Performed on the basis of the patient values, feedback to the control of fresh gas mixture is particularly efficient, especially when a patient circuit of FIG. 3 is used, which is based on the reuse of gas, as is typical in anaesthesia. Thereby exhalation gas is guided from the patient gas space 17 of the container 14 via a carbon dioxide absorber 36 into the patient's lungs 1a again. During inhalation, the flow into the lungs may temporarily be as high as 100 l/min, and even the average flow of adults equals about 20 to 30 l/min. Instead, the total flow mixed by the gas mixer equals at its minimum only the amount the patient consumes, i.e. about 200 ml/min of oxygen. In most cases, however, flows are 0.5 to 1 l/min in modern anaesthesia. As the total volume of a patient circuit including lungs may be 6 to 7. l, it takes a long time to effect a change in the concentration of the gas in the circuit takes a long time, and both the fresh gas concentration and the total flow may have to be regulated.

The above example shows also the difference between the oxygen concentration of exhalation measured from the patient, the controllable set value, the oxygen concentration mixed by the gas mixer and the set value of the device used in patient care. To maintain the above mentioned set value, e.g. 25%, and considering the oxygen consumption of a patient, the flow regulated by the gas mixer may, for example, be 200 ml/min of 100% oxygen.

The gas mixer also comprises an anaesthetic vaporizer 37. Controlled by the control unit 7b of the gas mixer, anaesthetic vapour is added to fresh gas by means of the anaesthetic vaporizer. The anaesthetic vapour control is on the one hand based on the internal sensors 38 of the gas mixer and on the patient measuring signal obtained from the gas monitor. Based on these facts, the control unit 7b of the gas mixer controls anaesthetic vapour by means of a valve 39. A diluting effect of the patient circuit that was described above for oxygen is correspondingly typical of anaesthetic vapour. Thus, feed-back from the measuring value of the patient is especially useful also when it comes to anaesthetic vapour.

The above embodiment is not intended to restrict the invention in any way, but the invention may be modified freely within the scope of the claims. Therefore, it is obvious that the arrangement of the invention or its details do not necessarily have to be the same as shown in the figures, but other solutions are possible, too. The invention can naturally also be applied in such a manner that inhalation gases of a patient are measured etc.

What is claimed is:

1. A system for use in monitoring and controlling the administration of an agent to a patient, the system comprising:

a controllable administration device (2,2a) adapted to affect a controllable parameter of the agent administered to the patient, the agent having a reference value in the atmosphere external of the system;

a measuring device (5,5a,5b) adapted to measure a characteristic of the agent dependent on the controllable parameter and to provide a measuring value for operating the controllable administration device;

an external measuring point for the measuring device, the external measuring point being outside the controllable administration device;

a transmission (21,22) link between the external measuring point and the measuring device;

a user interface (20) by which the controllable administration device can be controlled using set values;

a control unit (7,7a,7b) adapted to control the controllable administration device on the basis of the measuring value and the set values;

means for comparing the measuring value with the reference value; and the control unit being adapted to interrupt the control action of the controllable administration device when the measuring value attains the reference value of the agent.

2. The control system of claim 1 wherein the controllable administration device comprises a gas mixer.

3. The control system of claim 1 wherein the controllable administration device comprises a ventilator.

4. The control system of claim 2 wherein the gas mixer comprises an anaesthetic vaporizer.

5. The control system of claim 1 wherein the control system continues its operation when the measuring value attains the reference value of the agent by means of internal sensors.

6. The control system of claim 1 wherein when the measuring value attains the reference value of the agent, the system is adapted to use a different set value than when the measuring value differs from the reference value of the agent.

7. A method of controlling the administration of an agent to a patient, the method comprising the steps of:

providing a controllable administration device adapted to affect a controllable parameter of the agent administrated to the patient;

measuring a characteristic of the agent dependent on the controllable parameter at a measuring point external of the controllable administration device;

providing a measuring value from the measurement suitable for operating the controllable administration device;

providing a reference value of the agent in the ambient atmosphere;

comparing the measuring value with the reference value of the agent; and interrupting the control action of the controllable administration device when the measuring value obtains the reference value of the agent.

8. A system for controlling a parameter utilized in the care of a patient, the system using the same or a different parameter as a control parameter in the course of such control, the system comprising:

a control device (2, 2a) for establishing the parameter utilized in patient care;

a measuring device (5, 5a, 5b) adapted to measure a characteristic dependent on the parameter utilized in patient care at a measuring point outside of said control device, said measuring device providing a measured value of the parameter dependent characteristic;

a user interface (20) for generating a set value for the operation of the control device;

a control unit (7, 7a, 7b) adapted to control the control device on the basis of the measured value and set value for controlling the parameter utilized in patient care;

wherein the control parameter has a reference value in the atmosphere external of the system;

means for comparing the measured value of the parameter dependent characteristic with the reference value of the control parameter; and the control unit being adapted to interrupt the control action of the control device based on the measured value when the measured value attains the reference value.

9. A system as claimed in claim 8 wherein said system continues its operation when the measured value attains the reference value of the control parameter by means of internal sensors.

10. The control system as claimed in claim 8 wherein when said measured value attains the reference value of the control parameter, the system is adapted to use a different to use a different set value than when the measured value differs from the refernce value of the control parameter.

11. A method for controlling a parameter utilized in the care of a patient, said method comprising the steps of:

selecting a control parameter for controlling the parameter utilized in the care of the patient, the control parameter being the same as, or a different parameter, than that utilized in the care of the patient, the control parameter having a reference value in the ambient atmosphere;

providing a controllable device adapted to affect the control parameter;

measuring a characteristic dependent on the parameter utilized in patient care at a measuring point external of the controllable device and providing a measured value suitable for operating the controllable device;

comparing the measured value with the reference value; and interrupting the control action of the controllable device based on the measured value when the measured value obtains the reference value.

* * * * *